United States Patent [19]

Lines

[11] Patent Number: 5,531,773

[45] Date of Patent: Jul. 2, 1996

[54] METHOD AND APPARATUS FOR HANDLING ANIMALS

[75] Inventor: Lancelot H. Lines, Mount Bryan, Australia

[73] Assignee: Australian Meriono Wool Harvesting, LTD., Elizabeth Downs, Australia

[21] Appl. No.: 312,663

[22] Filed: Sep. 27, 1994

Related U.S. Application Data

[63] Continuation of Ser. No. 8,692, Jan. 25, 1993, abandoned.

[30] Foreign Application Priority Data

May 1, 1992 [AU] Australia .................. 15992/92

[51] Int. Cl.[6] ................................. A61N 1/18
[52] U.S. Cl. ........................... 607/046; 607/63
[58] Field of Search ................. 607/46, 48, 63, 607/72, 73, 115, 148, 68

[56] References Cited

U.S. PATENT DOCUMENTS

| | | |
|---|---|---|
| 4,141,259 | 2/1979 | Jacobsen et al. .......... 607/63 X |
| 4,237,896 | 12/1980 | Lines . |
| 4,256,116 | 3/1981 | Meretsky et al. . |
| 4,431,002 | 2/1984 | Maurer et al. .......... 607/46 |
| 4,759,368 | 7/1988 | Spanton et al. .......... 607/46 |
| 4,945,910 | 8/1990 | Budyko et al. .......... 607/46 |
| 4,949,721 | 8/1990 | Torin et al. . |
| 5,097,833 | 3/1992 | Campos .......... 607/68 |

FOREIGN PATENT DOCUMENTS

| | | |
|---|---|---|
| 561340 | 6/1982 | Australia . |
| 2099750 | 12/1982 | United Kingdom . |

*Primary Examiner*—George Manuel
*Assistant Examiner*—Jeffrey R. Jastrzab
*Attorney, Agent, or Firm*—Arthur F. Zobal

[57] ABSTRACT

Pain in an animal during animal husbandry procedures is blocked and tetany of the muscles caused by the application of spaced pulses of electrical current. The pulses are of minimum or zero width on initial application to the animal, and a gradual increase of pulse width cuases gradual increases in pain blockings until tetany occurs without distress to the animal.

22 Claims, 1 Drawing Sheet

METHOD AND APPARATUS FOR HANDLING ANIMALS

This is a continuation of application Ser. No. 08/008,692 filed Jan. 25, 1993, abandoned.

This invention relates to the handling of animals, particularly for the handling of animals for animal husbandry and veterinary purposes.

BACKGROUND OF THE INVENTION

Both large and small animals have to be handled for animal husbandry and veterinary purposes, and these animals include not only domestic and farm and station animals, but also feral and wild animals. Thus in these situations it is necessary to hold or restrain the animal, and conventionally this has been accomplished by manually handling the animal or by using mechanical means such as a crush or cradle or the like to physically restrain the animal. Also it is known to use drugs such as an anaesthetic to control the animal, but these drugs are often slow acting and on recovery the animal is often in a grave condition. Also unless care is taken it is possible to take the life of the animal by the careless use of drugs.

Also it is known to electrically immobilise animals, and Australian Patent No. 5561340 discloses a method and apparatus for producing a state of tetany in the animals muscles while leaving the organs in a relaxed condition by passing a pulsed electric current through the animals muscles. Reference is also made to U.S. Pat. No. 4,237,896 in this regard which is directed to a corresponding invention. The immobilisation of animals is achieved in a quick, safe manner so that operations such as dehorning, shearing, castration etc., and other forms of surgery may be carried out in the field or elsewhere in an efficient manner, with the minimum of physical effort being required to restrain the animal. The animal is immobilised by the passage of the small electric current through the nerve and muscle tissue thus causing tetany, that is the contraction of the muscles thus immobilising the animal and effecting the nervous system in such a way that the animal is not conscious of any pain when the current is applied.

There are also various patents relating to electro-anaesthesia, such as SU 1074543, SU 102277, SU 906579, SU 776613, U.S. Pat. No. 4,383,522 and FR 2457696, these being predominantly directed to human use. Also U.S. Pat. No. 4,256,116 describes the supplying of pulsing current to spaced electrodes in a patient, the current being supplied to the spaced electrodes in succession for pain relief.

SU 1435261 is directed to a post-operative analgesia method involving local treatment with a pulsing current with one electrode placed in the base of the wound and the other parallel to it and extending into the subcutaneous fat, While SU 1068127 describes the healing of post-operative wounds by the use of a sinusoidal current, the voltage being increased until the appearance of contraction of muscles in the wound area.

A pulse generator for a pain blocking bandage is disclosed in GB 2,099,705, in which there is provided a feedback circuit to supply spaced bursts of multiple pulses to the patient.

This invention embodies the same basic design and operational concepts as previous designs covered in our earlier patents such as AU 5561340 in that it consists essentially of a stable source of moderately high voltage to overcome typical electrical resistance in animal tissues, an oscillator controlling a switching transistor to deliver current pulses of a fixed duration at fixed intervals to the subject animal, and a current sensing device simultaneously controlling the switching transistor to enable the operator to control the amplitude of these current pulses.

Whilst this original design has been successfully manufactured and used throughout the world for many years, difficulty has sometimes been experience by operators in electing the most effective setting of current amplitude at switch-on for a given animal to give sufficient initial immobility without causing discomfort and distress.

Thus it would be highly desirable to be able to apply the apparatus and method to an animal without startling the animal, and to be able to further control the blockage of pain in an animal, and the present invention is directed to this end.

Experiments over many years have shown that providing a means of gradually increasing the amplitude of pulses from zero to the point of immobilisation has done nothing to improve the situation but rather tends to increase the level of discomfort felt by the animal, provoking violent movements potentially dangerous both to the operator and the animal itself.

SUMMARY OF THE INVENTION

It is an object of this invention to manipulate animals for routine husbandry practice as well as veterinary interventions, with safety to the operator and complete safety to the animal in a situation where there is pain block.

It has been found that there are two separate aspects to this condition:

1. Manipulation of the muscles.
2. Rendering the animal compliant and comfortable with the suppression of pain.

Both these aspects can be attained individually or collectively by suitable adjustments of the voltage, current and pulse width, as well as the placement of the needles or electrodes in the animal, and can be either partial or complete in their effect.

It has been found that muscle rigidity is a function of pulse width and current. At any suitable current setting, the muscle rigidity can be regulated by increasing the pulse width, and this is progressive. If the animal is in tetanized condition, breathing of the animal must be continually monitored, and the pulse width varied to allow the animal to breathe while maintaining the desired degree of tetany.

However where it is desired that the animal have a relaxed muscle condition with pain block, this can be achieved by use of a very short pulse width with a suitable current setting. Thus by beginning with a zero pulse width and gradually increasing the pulse width the animal can have complete pain block without tetany. This is obtained by a generalised stimulation of spinal chord afferent nerves using suitable needle placements, and so releasing the endogenous opioids and other nerve-transmitting substances.

This can reach a complete pain block if the current density on the spinal chord or part thereof, prevents messages reaching the brain by invoking the pain control mechanism involved in the Gate control theory of pain.

The position of the needles is important due to the relative conductivity of the tissue in which the needle is placed. It is a requirement that the needles be placed adjacent the spinal chord for complete pain block, and the effect is often determined by the conductivity of the adjacent tissue.

Optimum placements are (1) in the cheek area where there is a minimum of fat and is an area where conductivity through the foramina to the brain stem is optimised, and (2) adjacent the tail. In this respect it has been found that the best effect is achieved by placing the needle in the tail, especially three (3) vertebrae from the rump. This is an area where there is little fat and the current density is maximised on the spinal column because it the close proximity of the needle to the spinal column.

BRIEF STATEMENT OF THE INVENTION

Thus there is provided according to the invention a method of immobilising or controlling pain or providing a pain block in an animal undergoing husbandry without rendering the animal unconscious, including the step of applying spaced electrodes to the spinal column of the animal and supplying a pulsed current initially of zero or low pulse width to the electrodes, the duration of each pulse being small in relation to the spacing between the pulses, characterised in that the pulse width is gradually increased to a greater pulse width with corresponding increase in pain blockage until the desired degree of pain blockage is reached with corresponding immobilisation.

In a further aspect of the invention there is provided a method of immobilising or controlling pain or providing pain block in an animal to undergo husbandry without rendering the animal unconscious, said method including the step of applying spaced electrodes to the animal adjacent the spinal column, one of said electrodes being positioned in the tail adjacent the third vertebrae, and supplying a pulsed current initially of zero or low pulse width to the electrodes, the duration of each pulse being small in relation to the spacing between the pulses, characterised in that the pulse width is gradually increased to a greater pulse width with corresponding increase in pain blockage until the desired degree of pain blockage is reached with corresponding immobilisation.

Also there is provided according to the invention an apparatus for immobilising or controlling pain or providing pain block in an animal, said apparatus comprising a pair of electrodes, circuit means for generating and supplying low voltage spaced pulses to the electrodes, characterised in that said circuit means includes pulse width variable means to vary the width of the said pulses from zero or a low value to a desired value.

DESCRIPTION OF THE PREFERRED EMBODIMENT

Figure 1:
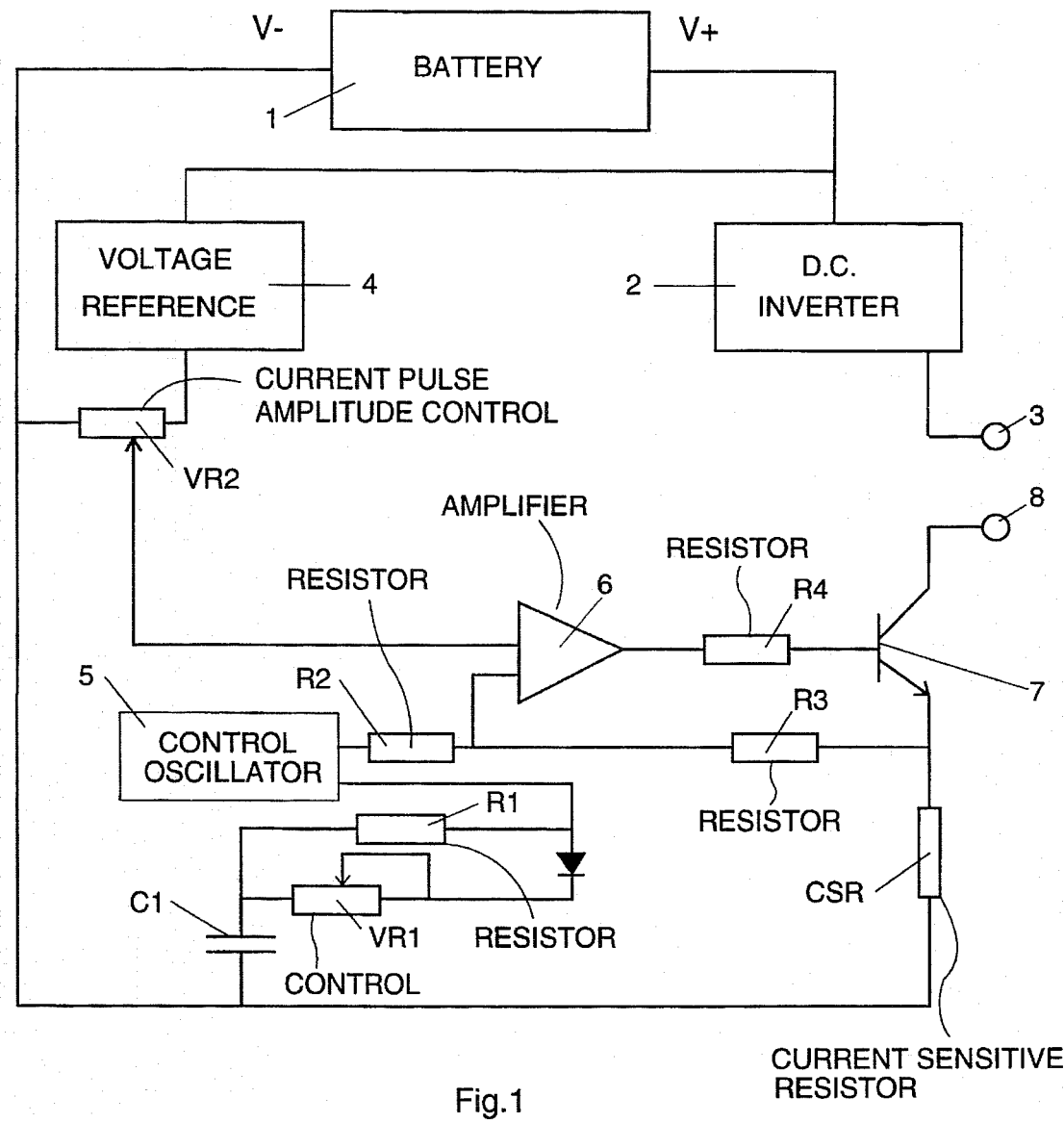
FIG. 1 illustrates one form of circuit embodied in the invention.

It has now been determined that the electrical current has two distinct effects, there is an effect on the nervous system and a separate effect on the muscular system. It was assumed previously that the application of the current had the effect that the animal was not aware of any pain, but it was not understood whether this was due solely to the tetany, or whether there was some other cause. However, it has now been found that the nervous system can be effected to such an extent that the animal is not aware of any pain, so that there is in effect produced a pain block. By reducing the pulse width to a figure such as 0.1 milliseconds or less it has been found that the nervous system is effected, and that on increasing the pulse width there is a progressive blockage of pain so that the animal is unaware of and does not sense any pain. Apparently the transmission of the electrical signals through the nervous system is effected and these signals are effectively blocked so that the animal is not aware of any pain.

With the animal in a condition where the nervous system is effected, the pulse width can be gradually increased from zero, and as the pulse width is increased a gradual stiffening of the muscles occurs, until at a pulse width of about 1.0 milliseconds complete tetany of the muscles occurs at which stage there is a complete blockage of pain.

Thus it has been found that at small pulse widths, the nervous system is effected, while at greater pulse widths the muscular system is also effected.

In order to carry out veterinary work and animal husbandry on an animal, it is highly desirable for obvious reasons that the animal be wholly or partially immobilised. A potential of up to 40 or 55 volts and a current in the order of 50 milliamperes will immobilise a sheep, the current being in pulses of 50 Hertz, each pulse being of 1 millisecond and spaced 20 milliseconds apart. In order to immobilise cattle, the current can be increased up to about 300 milliamperes.

However with the present invention the voltage can be in the order of 40 to 70 volts with the initial application of the current at a small pulse width in the order of zero to 0.1 milliseconds, and then the pulse width can be increased until the desired level of pain blockage is achieved. This can be any level up to the level at which tetany occurs, the upper limit being in the order of 1.0 to 1.5 milliseconds. Also the spacing of the pulses can be in the range of 10 to 30 milliseconds apart.

It has been found that with one electrode applied to the centre of the spine and the other at the tail, that pain blockage and tetany can be obtained at the rear quarters of the animal, while the forequarters are totally unaffected. With the initial application of a very small pulse width the animal is not startled, does not stamp its feet, or bellow (in the case of a calf or cattle). With gradual increase of pulse width there is a progressive pain block until tetany occurs. Animals have had only the hind-quarters immobilised, and been fire branded on the hind-quarters with no visible symptoms of pain, ie. no bellowing or movement of the forelegs.

With small animals, including pets such as cats and small dogs, where there is little body bulk and fat tissue the voltage required can be as low as 5 to 10 volts, this being sufficient to drive the current through the tissues of the animal. The current can be minimal, and be virtually as low as zero.

Thus animal husbandry can be carried out on the animal without pain by the use of a very small pulse width where tetany is not required or necessary. However with some animals it may be desirable to use a tranquilliser to quieten the animal prior to and during the application of the electrodes for the electrical current. This is so that the animal, particularly a wild, feral or range animal, can be easily handled, and also so that the animal is not unduly frightened by the presence of people in the vicinity of the animal. The use of the tranquilliser would be of a dose sufficient to quieten the animal only and would not have to be of a dosage to cause medical problems to the animal.

The variation of the pulse width can either be automatically or manually controlled, and reference is now made to the accompanying drawing which shows one example of a manual control.

In the drawing which shows a form of circuit for the apparatus of the invention, there is provided a 6 V dry battery 1, the positive of which is connected to a regulated 50 volt D.C. inverter 2 the output of which is connected to one terminal 3 of the immobilising output. Also there is connected in circuit a precision low voltage reference 4 and a current pulse amplitude control VR2.

A pulse width control oscillator 5 is controlled by VR1, there also being included a current pulse amplitude operational amplifier 6 connected to the base of a main switching transistor 7 connected to other terminal 8 of the immobilising output. Also included is a current sensitive resistor CSR and other suitable resistors R1, R2, R3, and R4.

As shown the pulse width control may be a comparator set up as an asymmetrical oscillator, with the repetition rate set by the timing components R1 and C1. The pulse width is set by the timing components R1, VR1 via a diode and C1, thus giving the operator external control of the pulse width. VR2 simply provides the usual external control for initially setting the required pulse amplitude.

Thus it will be seen that there is provided according to the invention a method of producing in an animal a pain block, or a method of rendering the animal immune to the pain of animal husbandry, by applying to the animal a pulsed electrical current in which the pulse width is initially of a value sufficient to effect the nervous system so that the animals sense of pain is at least diminished, and on increasing the pulse width there is a diminishing sense of pain by the animal accompanied by immobilisation.

When the machine is turned off, recovery is instantaneous and complete. This is compared with chemical anaesthesia when animals fall down and extensive bruising and even broken limbs can occur as well as the time involved to get the animal on its feet. The appetite of the animal is often affected for hours and even days by the use of chemicals By this invention, total freedom from chemical residues is ensured, which residues have become a major concern in the meat, milk and velvet industries.

While a preferred embodiment of the invention has been described, the invention is not to be limited thereto, but can include variations falling within the spirit and scope of the invention.

I claim:

1. A method of controlling pain or providing a pain block and immobilization in an animal undergoing husbandry without rendering the animal unconscious, wherein the animal is of the type having a spinal column, comprising the steps of applying spaced electrodes to the animal, with at least one electrode located near the spinal column of the animal, and supplying to the electrodes as a function of time a current of spaced apart pulses of relatively low voltage, each of said pulses having a width which is small in relation to the spacing between the pulses, and gradually varying the widths of the pulses from initial small or zero pulse widths to greater pulse widths with corresponding increase in pain blockage until the desired degree of pain blockage is reached with accompanying immobilization.

2. A method of controlling pain or providing a pain block in an animal as defined in claim 1 in that the small pulse widths produced are in the order of zero to 0.1 milliseconds.

3. A method of controlling pain or providing a pain block in an animal as defined in claim 2 wherein said voltage supplied is in the range of 5 to 70 volts, said current supplied is in the range of 0 to 300 milliamperes and the pulses are spaced 10 to 30 milliseconds apart.

4. A method of controlling pain or providing a pain block in an animal as defined in claim 1 in that the said greater pulse widths produced are in the order of 1.0 to 1.5 milliseconds.

5. A method of controlling pain or providing a pain block in an animal as defined in claim 4 wherein said voltage supplied is in the range of 5 to 70 volts, said current supplied is in the range of 0 to 300 milliamperes and the pulses are spaced 10 to 30 milliseconds apart.

6. A method of controlling pain or providing a pain block in an animal as defined in claim 1, wherein said voltage supplied is in the range of 5 to 70 volts, said current supplied is in the range of 0 to 300 milliamperes and the pulses being spaced 10 to 30 milliseconds apart.

7. The method of claim 1, wherein:

all of said pulses of current have substantially the same amplitude.

8. The method of claim 1, wherein:

said pulses are applied to said electrodes at a fixed repetition rate.

9. The method of claim 8, wherein:

all of said pulses of current have substantially the same amplitude.

10. A method of controlling pain or providing a pain block and immobilization in an animal to undergo husbandry without rendering the animal unconscious, wherein the animal is of the type having a spinal column, a rump, and a tail, said method comprising the steps of applying spaced electrodes to the animal adjacent the spinal column, one of said electrodes being positioned in the tail of the animal, supplying to the electrodes as a function of time, a current of spaced apart pulses of relatively low voltage, said pulses being initially of zero or low pulse widths, the time duration of each pulse being small in relation to the spacing between the pulses, and gradually increasing the pulse width of said pulses with corresponding increase in pain blockage until the desired degree of pain blockage is reached with corresponding immobilization.

11. The method of claim 10 wherein the initial pulse widths are in the order of zero to 0.1 milliseconds.

12. The method of claim 11 wherein said increased width pulses have widths not greater than about 1.5 milliseconds.

13. The method of claim 12, wherein said voltage supplied is in the range of 5 to 70 volts, said current supplied is in the range of 0 to 300 milliamperes and the pulses are spaced 10 to 30 milliseconds apart.

14. A method of controlling pain or providing a pain block and immobilization in an animal undergoing husbandry without rendering the animal unconscious, wherein the animal is of the type having a spinal column, comprising the steps of applying spaced electrodes to the animal near the spinal column of the animal and applying to the electrodes as a function of time a current of spaced apart pulses of relatively low voltage such that an initial series of pulses of current and subsequent series of pulses of current are applied to said electrodes, each pulse having a width which is small in relation to the spacing between the pulses, after said initial series of pulses is applied to said electrodes gradually increasing the widths of the subsequent series of pulses such that the pulses of each subsequent series of pulses have increased pulse widths, with corresponding increase in pain blockage until the desired degree of pain blockage is reached with accompanying immobilization.

15. The method of claim 14, wherein:

said animal is of the type having a spinal column, a rump, and a tail with at least three vertebrae from the rump, one of said electrodes is positioned in the tail of the animal adjacent the third vertebrae.

16. The method of claim 14, wherein:

said electrodes are positioned in the animal adjacent the spinal column of the animal.

17. A method of controlling pain or providing a pain block and immobilization in an animal undergoing husbandry without rendering the animal unconscious, wherein the animal is of the type having a spinal column, comprising the steps of applying spaced electrodes to the animal, with at least one electrode located near the spinal column of the animal, and applying to the electrodes as a function of time a current of spaced apart pulses of relatively low voltage such that an initial series of pulses of current and subsequent series of pulses of current are applied to said electrodes, after said initial series of pulses is applied to said electrodes gradually increasing the widths of the pulses such that the pulses of each subsequent series of pulses have increased pulse widths, with corresponding increase in pain blockage until the desired degree of pain blockage is reached with accompanying immobilization.

18. The method of claim 17, wherein:

said one electrode is applied to the animal adjacent the spinal column.

19. The method of claim 17, wherein:

all of said pulses of current have substantially the same amplitude.

20. The method of claim 17, wherein:

said pulses are applied to said electrodes at a fixed repetition rate.

21. The method of claim 20, wherein:

all of said pulses of current have substantially the same amplitude.

22. The method of claim 17 wherein said animal is a lower animal as distinguished from a human being.

* * * * *